| (12) | United States Patent | (10) Patent No.: | US 8,822,206 B2 |
|---|---|---|---|
| | Levchenko et al. | (45) Date of Patent: | Sep. 2, 2014 |

(54) DEVICE FOR HIGH-THROUGHPUT STIMULATION, IMMUNOSTAINING, AND VISUALIZATION OF SINGLE CELLS

(75) Inventors: Andre Levchenko, Ellicott City, MD (US); Raymond Cheong, Baltimore, MD (US); Chiaochun J. Wang, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 1145 days.

(21) Appl. No.: 12/083,482

(22) PCT Filed: Oct. 11, 2006

(86) PCT No.: PCT/US2006/039959
§ 371 (c)(1),
(2), (4) Date: Apr. 16, 2009

(87) PCT Pub. No.: WO2007/044856
PCT Pub. Date: Apr. 19, 2007

(65) Prior Publication Data
US 2010/0028928 A1 Feb. 4, 2010

Related U.S. Application Data

(60) Provisional application No. 60/725,415, filed on Oct. 11, 2005.

(51) Int. Cl.
*B01L 1/00* (2006.01)
*B01L 3/00* (2006.01)
*B01L 7/00* (2006.01)
*G01N 15/14* (2006.01)

(52) U.S. Cl.
CPC ............... *B01L 3/5025* (2013.01); *G01N 15/14* (2013.01); *B01L 2300/0816* (2013.01); *B01L 2200/06* (2013.01); *B01L 2300/0864* (2013.01); *B01L 2400/0487* (2013.01); *B01L 7/00* (2013.01)
USPC ................. 435/288.5; 435/286.5; 435/287.1; 435/288.3; 435/288.4; 435/305.1; 435/305.2

(58) Field of Classification Search
CPC ................ B01L 2300/0864; B01L 2300/0816; B01L 2300/0861; B01L 2200/06; B01L 2200/0647; B01L 3/5027; B01L 2400/0487; B01L 3/5025; B01L 7/00; G01N 15/14
USPC .......... 435/286.5, 287.1, 288.3, 288.4, 288.5, 435/305.2, 305.1
See application file for complete search history.

(56) References Cited

U.S. PATENT DOCUMENTS

| 5,376,252 A | 12/1994 | Ekstrom et al. |
|---|---|---|
| 5,876,946 A | 3/1999 | Burbaum et al. |

(Continued)

FOREIGN PATENT DOCUMENTS

WO WO-0218952 A2 * 3/2002

OTHER PUBLICATIONS

Yun et al., "Micro/Nanofluidic Device for Single-Cell-Based Assay", *Biomedical Microdevices* 7:1, 35-40 (2005).

(Continued)

*Primary Examiner* — Nathan Bowers
(74) *Attorney, Agent, or Firm* — Ward and Smith, P.A.

(57) ABSTRACT

Cell stimulation, staining, and visualization are common techniques in both clinical and research settings. The invention is directed to microfluidic devices for in situ cell stimulation, staining, and/or visualization, and related methods for applying one or more stimuli to the cells, and fixing and staining of cells in situ. The device allows for high-throughput screening of living cells using a minimal quantity of reagents where the fate of individual cells can be followed over time.

19 Claims, 1 Drawing Sheet

(56) References Cited

U.S. PATENT DOCUMENTS

| | | | |
|---|---|---|---|
| 5,942,443 | A | 8/1999 | Parce et al. |
| 5,989,835 | A | 11/1999 | Dunlay et al. |
| 6,071,478 | A | 6/2000 | Chow |
| 6,086,740 | A | 7/2000 | Kennedy |
| 6,238,538 | B1 | 5/2001 | Parce et al. |
| 6,274,337 | B1 | 8/2001 | Parce et al. |
| 6,306,659 | B1 | 10/2001 | Parce et al. |
| 6,395,232 | B1 | 5/2002 | McBride |
| 6,399,952 | B1 | 6/2002 | Maher et al. |
| 6,408,878 | B2 | 6/2002 | Unger et al. |
| 6,429,025 | B1 | 8/2002 | Parce et al. |
| 6,479,299 | B1 | 11/2002 | Parce et al. |
| 6,488,895 | B1 | 12/2002 | Kennedy |
| 6,551,841 | B1 | 4/2003 | Wilding et al. |
| 6,573,039 | B1 | 6/2003 | Dunlay et al. |
| 6,585,939 | B1 | 7/2003 | Dapprich |
| 6,614,030 | B2 | 9/2003 | Maher et al. |
| 6,620,591 | B1 | 9/2003 | Dunlay et al. |
| 6,632,656 | B1 | 10/2003 | Thomas et al. |
| 6,653,124 | B1 | 11/2003 | Freeman |
| 6,716,588 | B2 | 4/2004 | Sammak et al. |
| 6,727,071 | B1 | 4/2004 | Dunlay et al. |
| 6,759,206 | B1 | 7/2004 | Rubin et al. |
| 6,818,435 | B2 | 11/2004 | Carvalho et al. |
| 6,829,753 | B2* | 12/2004 | Lee et al. ............ 716/30 |
| 6,838,680 | B2 | 1/2005 | Maher et al. |
| 6,857,449 | B1 | 2/2005 | Chow |
| 6,875,578 | B2 | 4/2005 | Giuliano et al. |
| 6,951,632 | B2 | 10/2005 | Unger et al. |
| 7,005,292 | B2 | 2/2006 | Wilding et al. |
| 7,018,830 | B2 | 3/2006 | Wilding et al. |
| 7,040,338 | B2 | 5/2006 | Unger et al. |
| 7,060,445 | B1 | 6/2006 | Dunlay et al. |
| 7,067,263 | B2 | 6/2006 | Parce et al. |
| 7,117,098 | B1 | 10/2006 | Dunlay et al. |
| 7,143,785 | B2 | 12/2006 | Maerkl et al. |
| 7,160,687 | B1 | 1/2007 | Kapur et al. |
| 7,216,671 | B2 | 5/2007 | Unger et al. |
| 7,223,363 | B2* | 5/2007 | McNeely et al. ......... 422/417 |
| 7,235,373 | B2 | 6/2007 | Dunlay et al. |
| 7,376,256 | B2 | 5/2008 | Kirsch et al. |
| 7,378,280 | B2 | 5/2008 | Quake et al. |
| 7,452,726 | B2 | 11/2008 | Chou et al. |
| 7,476,363 | B2 | 1/2009 | Unger et al. |
| 7,494,555 | B2 | 2/2009 | Unger et al. |
| 7,601,270 | B1 | 10/2009 | Unger et al. |
| 7,939,018 | B2* | 5/2011 | Bedingham et al. ......... 422/64 |
| 2004/0115838 | A1* | 6/2004 | Quake et al. ............ 436/538 |
| 2005/0217750 | A1* | 10/2005 | Jeon et al. ............ 141/9 |
| 2006/0134599 | A1* | 6/2006 | Toner et al. ............ 435/4 |
| 2006/0194273 | A1 | 8/2006 | Thomas |
| 2007/0110631 | A1* | 5/2007 | Ajdari et al. ............ 422/100 |
| 2007/0196912 | A1 | 8/2007 | Facer et al. |
| 2009/0239292 | A1 | 9/2009 | Thomas et al. |
| 2010/0035292 | A1 | 2/2010 | Levchenko et al. |

OTHER PUBLICATIONS

Gu et al., "Computerized Microfluidic Cell Culture Using Elastomeric Channels and Braille Displays", *PNAS*, vol. 100, No. 45, 15861-15866 (2004).

Thorsen et al., "Microfluidic Large-Scale Integration", *Science Magazine*, vol. 298, p. 580-584 (2002).

Unger et al., "Monolithic Microfabricated Valves and Pumps by Multilayer Soft Lithography", *Science Magazine*, vol. 288, p. 113-116 (2000).

R. Cheong, C. J. Wang, and A. Levchenko, Using a microfluidic device for high-content analysis of cell signaling. Science Signaling 2:75, p. 5-18 (Jun. 16, 2009).

S. Paliwal, P.A. Iglesias, K. Campbell, Z. Hilioti, A. Groisman, and A. Levchenko, MAPK-mediated biomodal gene expression and adaptive gradient sensing in yeast. Nature 446, p. 46-51 (Mar. 1, 2007).

R. Cheong, S. Paliwal and A. Levchenko, High-content screening in microfluidic devices. Expert Opin. Drug Discov. 5:8, p. 715-720 (2010).

B.W. Roberts and W.L. Olbricht, The distribution of freely suspended particles at microfluidic bifurcations. Separations 52:1, p. 199-206 (Jan. 2006).

R. Cheong, C.J. Wang, and A. Levchenko, High content cell screening in a microfluidic device. Mol Cell Proteomics 8 (3), p. 433-442 (Oct. 24, 2008).

B.W. Roberts, W.L. Obricht. "Flow-induced particulate separations." AIChE Journal 11(49):2842-2849 (2003).

D.D. Carlo, L.Y. Wu, L.P. Lee. "Dynamic single cell culture array." Lab on a Chip 6:1445-1449 (2006).

A. Tourovskaia, X. Figueroa-Masot, A. Folch. "Differentiation-on-a-chip: A microfluidic platform for long-term cell culture." Lab on a Chip 5:14-19 (2005).

R. Gomez-Sjoberg, Anne A. Leyrat, Dana M. Pirone, Christopher S. Chen, and Stephen R. Quake, "Versatile, Fully Automated, Microfluidic Cell Culture System," Anal. Chem 2007, 79, 8557-8563.

Atsushi Kaneda, Chiaochun J. Wang, Raymond Cheong, Winston Timp, Patrick Onyango, Bo Wen, Christine A. Iacobuzio-Donahue, Rolf Ohlsson, Rita Andraos, Mark A. Pearson, Alexei A. Sharov, Dan L. Longo, Minoru S. H. Ko, Andre Levchenko, and Andrew P. Feinberg, "Enhanced sensitivity to IGF-II signaling links loss of imprinting of IGF2 to increased cell proliferation and tumor risk", PNAS, Dec. 26, 2007, 20926-20931, vol. 104, No. 52.

Matthew Fosbrink, Nwe-Nwe Aye-Han, Raymond Cheong, Andre Levchenko, and Jin Zhang, "Visualization of JNK activity dynamics with a genetically encoded fluorescent biosensor", PNAS, Mar. 23, 2010, 5459-5464, vol. 107, No. 12.

\* cited by examiner

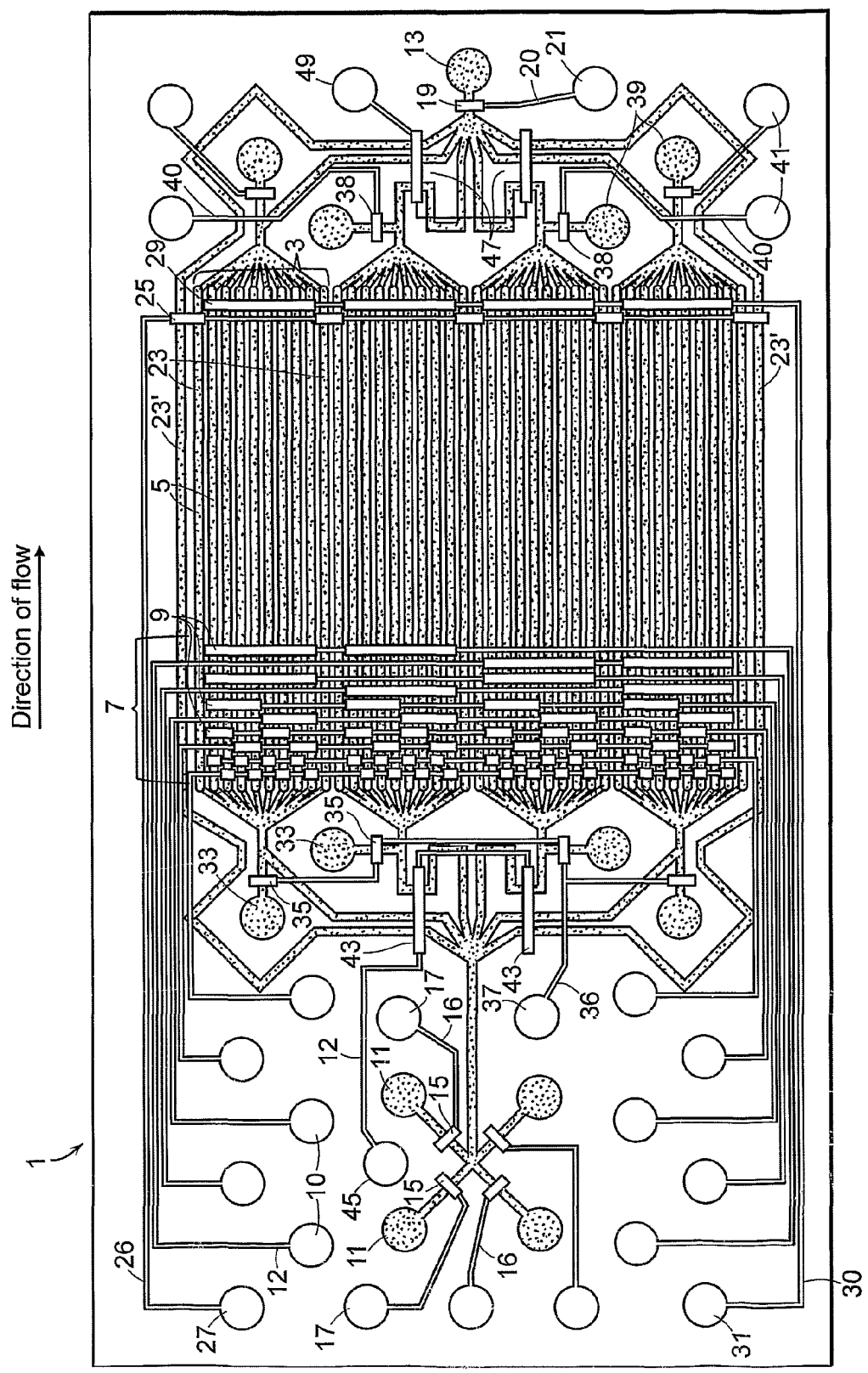

DEVICE FOR HIGH-THROUGHPUT STIMULATION, IMMUNOSTAINING, AND VISUALIZATION OF SINGLE CELLS

RELATED APPLICATIONS

This application claims the benefit of U.S. Provisional Application No. 60/725,415 filed Oct. 11, 2005, having the same title as the instant application. The entire contents of the aforementioned application are hereby incorporated herein by reference.

FIELD OF THE INVENTION

The present invention relates to microfluidics devices and methods for their use, including cell stimulation, staining, and/or visualization. More particularly, the invention relates to devices and methods for applying one or more stimuli to living cells, in parallel, and fixing, staining and/or visualizing cells in situ.

BACKGROUND OF THE INVENTION

Cell stimulation, staining, and visualization are common techniques in both clinical and research settings. Cell stimulation and staining methods frequently involve the use of antibodies or other reagents that are expensive or available in limited quantities. Immunofluorescence staining is typically performed on cells adhered to glass slides, resulting in the need for a large volume of reagents. Moreover, cell stimulation and staining are frequently performed in parallel under a number of different conditions (e.g., time course, active agent, or antibody used). Such complex methods also make such cell assays labor intensive and low throughput.

Fluorescence activated cell sorting (FACS) and enzyme linked immunosorbent assay (ELISA) allow for screening of a large number of cells under a variety of conditions, frequently using smaller volumes or quantities of reagents than are required for immunofluorescence staining of cells on tissue culture slides. However, cells can only be sorted and observed as a group using both FACS and ELISA. Single cells cannot be tracked over time, as is possible using microscopy.

In order to track single cells over time in response to various conditions, a microfluidic device for fast and parallel single-cell based assays has been developed (Yun and Yoon 2005. *Biomed. Microdev.* 7:35-40). The device is designed to passively capture single cells or beads on multiple cell positioning sites by a pre-defined fluidic stream. The apparatus allows for the injection of specific reagents into each isolated single cell. Each cell is "captured" and held in place covering a hook shaped drain channel that allows the capture of single cells. Drugs or other agents can be injected through the drain channel and responses of single cells can be watched over time. It is not known what stress pathways might be activated by the positioning of the cell in the top of the drain channel or how long a cell would be viable under such conditions.

An elastomeric device has been developed for studying cell fate that allows for cell culture in an array of individual microwells (Chin et al., 2004. *Biotechnol. and Bioeng.* 88:399-415). Cells are located within individual wells that are all exposed to the same media. Therefore, although individual cells can be tracked over time, they are all exposed to the same stimuli.

Elastomeric devices have been developed for use in biological studies (for review see Sia and Whitesides 2003. *Electrophoresis* 24:3563-3576). Such devices are can be biocompatible and can be prepared relatively easily and inexpensively by methods well known to those skilled in the art (See e.g., reviews Whitesides et al., 2001. *Ann. Rev. Biomed. Eng.* 3:335-373, incorporated herein by reference).

Methods for fabrication of higher order structures to control fluid flow have also been developed. Unger et al. (2000. *Science* 288:113-116, incorporated herein by reference) demonstrated that elastomeric layers could be readily assembled to create channels regulated by elastomeric valves. Using such a layered design, miniaturized, elastomeric, computer-controlled microfluidics devices have been developed. Thorsten et al. (2002, *Science* 298:580-584, incorporated herein by reference) teach a high-density microfluidic silicone chip containing plumbing networks with thousands of binary, micromechanical valves, and hundreds of individually addressable chambers. Although fluids can be loaded and mixed using the device, it is not large enough to accommodate eukaryotic cells and seeding of cells with an even distribution would not be possible using the device. Moreover, precise control of fluid flow through channels is somewhat limited.

Gu et al. (2004, *PNAS* 101:15861-15866) teach a computerized microfluidic cell culture apparatus using elastomeric channels and Braille displays to control flow of fluids from reservoirs for patterning or mixing. This simplifies the fabrication of the device, but substantially limits the number of channels that can be accessed through single ports, and limits the density of the valves in the device, both of which decrease the throughput of the device.

There is a need for a device and method to allow for high throughput screening of living cells using a minimal quantity of reagents wherein the fate of individual cells can be followed over time.

SUMMARY OF THE INVENTION

The invention is directed to microfluidic devices for in situ cell stimulation, staining, and/or visualization, and related methods for applying one or more stimuli to the cells, and fixing and staining of cells in situ. The devices preferably include a plurality of parallel fluid channels that are individually addressable by the opening and closing of a defined series of valves in a multiplexer, wherein the channels are operably connected to one or more ports. Preferably each channel is connected to at least one inlet port and one outlet port. The devices can be composed of biocompatible materials such as polydimethylsulfoxide (PDMS) or other elastomeric compound. In a preferred embodiment, the devices are preferably optically clear, biocompatible, gas permeable, and reversibly mountable to a solid support, such as a glass coverslip, so that the device can be cleaned and reused.

The invention includes the use of microfluidic devices in methods for in situ cell stimulation, staining, and/or visualization. A method for the use of the device includes introducing a plurality of cells through an inlet port into a plurality of parallel fluid channels wherein the inlet port is operably connected to the parallel fluid channels which are operably connected to at least one outlet port, and flow through the parallel fluid channels is controlled by a multiplexer that allows for each of the parallel fluid channels to be individually addressable; actuating a first selection of valves in the multiplexer to allow for differential fluid flow through the parallel fluid channels; introducing a first fluid into the microfluidics device through at least one inlet port; actuating a second selection of valves in the multiplexer that are distinct from the first selection of valves in the multiplexer; and introducing a second fluid into the microfluidics device through at least one inlet port. In a preferred method, the microfluidics device is used for cell stimulation, immunostaining, and/or visualization of single cells.

DESCRIPTION OF THE DRAWING

FIG. 1 is a schematic view of a microfluidics device according to the invention.

DEFINITIONS

The instant invention is most clearly understood with reference to the following definitions.

A "fluid layer" is any layer of a device in which fluid channels are incorporated. In the context of the instant invention, the fluid layer is typically the bottom layer of the device. In FIG. 1, the fluid layer is indicated by a stippled texture.

A "fluid channel" is a channel through which fluid and/or air can flow wherein the channel is part of the fluid layer. Fluid channels are functionally connected to both inlet and outlet ports optionally by connection through other fluid channels. Fluid channels are preferably rounded to improve sealing of the fluid channels by valves.

A "parallel fluid channel" is a channel within the device that is individually addressable by use of one or more valves. Preferably, a parallel fluid channel is a component of a reaction unit wherein flow through the parallel control channels is controlled by the multiplexer. In a preferred embodiment, the parallel fluid channels have a rectangular footprint of about 250 microns in width and about 1.3 cm in length with a parabolic cross section that is about 30 microns tall. The resulting channel is about 76 nl in volume.

"Individually addressable" means that control through each fluid channel, more specifically each parallel fluid channel, can be isolated from flow through all of the other channels in the device by actuating a specific valve or selection of valves.

A "reaction unit" is a unit by which the microfluidic device of the invention can be organized. A reaction unit preferably includes at least an inlet port and an outlet port operably connected to a series of parallel fluid channels through which flow is controlled by a multiplexer.

A "multiplexer" is a series of valves that allow for the parallel fluid channels to be individually addressable.

A "control layer" is the layer in which controllers, control channels, and valves are incorporated. It is typically embodiment of the invention, the control layer is the top layer of the device. The control layer is shown in FIG. 1 with no fill.

A "valve" is a component of the device that regulates flow through a fluid channel of the device by substantially inhibiting flow through the fluid channel upon actuation. Substantially inhibiting the flow means that flow is inhibited at least 80%, preferably at least 90%, more preferably at least 95%, even more preferably at least 99%, most preferably flow is completely (i.e., 100%) inhibited. In a preferred embodiment, a valve is a portion of a closed channel (i.e., open on one end only at a control layer inlet) in the control layer. A valve is located adjacent to, typically above, a channel in the fluid layer and is sufficiently wide to inhibit, preferably close off, flow through the adjacent fluid channel. The size of the valve is dependent on the size and shape of the fluid channel and the desired amount of pressure applied to actuate the valve. In a preferred method, the fluid channel is about 250 micron wide and the valve is about 300 micron wide. The channel and control valve cross perpendicularly. Upon actuation of the valve, preferably by hydrostatic pressure, the channel closes.

A "valve controller" or "controller" is the opening in the control layer at the end of a control channel, distal from the valve(s), that can be operably linked to a device (e.g., a fluid filled syringe) to modulate the pressure in the control channel.

A "control channel" operably links a valve controller to its valve(s). A control channel is sufficiently narrow (about 80 microns wide when the channels are about 250 microns wide) so that actuation of the linked valve(s) through the valve controller does not substantially interfere with fluid flow in the fluid channels adjacent to the control channel. The critical ratio of the width of the control channel to the fluid channel may also depend on the height of the fluid channel and the thickness of the bottom layer, however, the ratio of the control to fluid channel is preferably about less than 0.25 to not substantially interfere with flow. Substantially interfere is understood as not decreasing fluid flow by more than 50%, preferably not decreasing fluid flow by more than 40%, more preferably not decreasing fluid flow by more than 30%, even more preferably not decreasing fluid flow by more than 20%, most preferably not decreasing fluid flow by more than 10%.

An "elastomeric compound" or "elastomer" is a rubber. Preferred elastomers of the instant invention are biocompatible, gas permeable, optically clear elastomers useful in soft lithography including silicone rubbers, most preferably PDMS. Other possible elastomers for use in the devices of the invention include, but are not limited to, polyisoprene, polybutadiene, polychloroprene, polyisobutylene, poly(styrene-butadiene-styrene), the polyurethanes, and silicone polymers; or poly(bis(fluoroalkoxy)phosphazene) (PNF, Eypel-F), poly(carborane-siloxanes) (Dexsil), poly(acrylonitrile-butadiene) (nitrile rubber), poly(1-butene), poly(chlorotrifluoroethylene-vinylidene fluoride) copolymers (Kel-F), poly(ethyl vinyl ether), poly(vinylidene fluoride), poly(vinylidene fluoride-hexafluoropropylene) copolymer (Viton), elastomeric compositions of polyvinylchloride (PVC), polysulfone, polycarbonate, polymethylmethacrylate (PMMA), and polytertrafluoroethylene (Teflon).

A "compound to modulate cell adhesion" includes natural compounds, such as an extracellular matrix (ECM) component including, but not limited to, a proteins (e.g., fibronectin, laminin, integrin, collagen), peptides (e.g., RGD binding site), or other compounds (e.g., extracellular signaling molecule) present in the ECM that control cell attachment and/or migration. Non-ECM compounds (e.g., poly-lysine, gelatin, antibodies, carbohydrates) are also known to modulate cell adhesion. Compounds that modulate cell adhesion may also have other functions (e.g., modulating cell differentiation and/or signaling pathways). Compounds to modulate cell adhesion in the instant invention preferably promote cell adhesion. Compounds can be used to promote adhesion of both adherent and non-adherent cells. Selection of compounds to modulate cell adhesion are within the ability of those of ordinary skill in the art.

An "active agent" includes, but is not limited to, a naturally or non-naturally occurring molecule including agonists, antagonists, chemoattractants, chemorepellants, nutrient sources, mating factors, signal transduction molecules, growth factors, peptides, carbohydrates, nucleic acids, and drugs or therapeutic agents.

"In situ cell analysis" includes the study of cells in a microfluidics device of the invention wherein analysis includes stimulation, staining, and/or visualization of the cells preferably in response to active agents and growth conditions.

DETAILED DESCRIPTION OF THE INVENTION

The invention is directed to a microfluidics devices for in situ cell stimulation, staining and/or visualization. The device is composed of an optically clear, gas permeable, biocompatible polymer, such as PDMS, and reversibly mounted to a glass support, such as a cover slip, so that the cells can be visualized in situ. Reversible mounting allows for the device to be cleaned and re-used. The device can also be mounted to a heater to maintain the temperature of the device during the cell stimulation process. During live cell imaging, a stage warmer can be used. The device can also be mounted to a reservoir containing fresh growth media for cells for long term (i.e., longer than about one day) maintenance in the device. Such devices are well known to those skilled in the art.

The device is composed of two layers, a fluid layer and a control layer. The fluid layer is adjacent to the glass support. Typically, when cells are seeded into the device, they attach to the glass support on which the device is mounted. The fluid channels are rounded for optimal function of the valves. All fluid channels are flow through channels, operably connected to both an inlet and an outlet port, optionally by other fluid channels. The geometry of the parallel fluid channels in conjunction with sacrificial channels allows for even seeding of cells and fluid flow through the device. This makes the control of fluid flow more precise as compared to previous microfluidics devices.

Flow through the channels is controlled by valves present in the control layer. The valves in the control layer are operably linked to controllers via control channels. Control channels are one way channels. They terminate within the control layer and are accessed by a single port (i.e., the controller). One or more valves can be controlled by a single controller by operably linking the valves to a single control channel, or a valve can be of a dimension such that control of fluid flow through more than one fluid channel is modulated by actuation of a single controller. The use of a series of valves that control fluid flow through more than one fluid channel in the device of the invention allows for the device of the invention to be high throughput.

The device includes a series of parallel fluid channels operably connected to at least one inlet port and at least one outlet port. The preferred parallel array of fluid channels in the devices of the instant invention facilitate automated imaging of the device, further increasing the throughput of the methods of the invention. Fluid flow is controlled through the parallel fluid channels by a series of valves organized into a multiplexer. The multiplexer provides a structure and method to make each of the parallel fluid channels individually addressable. The device allows for precise control of fluids through the chambers which allows for the use of the device for high throughput cell stimulation, staining, and/or visualization.

A representative example of the device of the instant invention is shown in FIG. 1. It is understood that a plurality of an element may exist in the device when only one of the element is noted herein or in the drawing. Moreover, not all named elements are indicated by numbers at each occurrence in the drawing.

The device 1 of the invention includes at least one reaction unit 3 including a plurality of channels 5 through which flow of material is controlled by a multiplexer 7. The flow layer is shown with a stippled texture. FIG. 1 shows an exemplary device with four reaction units. The number of reaction units present in the device and the number of parallel fluid channels per reaction unit is not a limitation of the invention. In a preferred embodiment, the device includes four reaction units each having eight parallel fluid channels for cell analysis and testing, and two sacrificial channels equalize the distribution of cells in the channels in which cell analysis and testing is done. Sacrificial channels also allow fluid between the inlet and reaction unit to be purged. The direction of flow of material in the device is indicated.

The multiplexer includes a plurality of channel valves 9 each of which controls the flow of material through at least one channel. A valve may also control the flow of material through multiple channels that may or may not be adjacent to each other, and may or may not be in a single reaction unit. The valves are controlled by a plurality of channel valve controllers 10. Controllers are operably connected to valves through control channels 12. The cross section of the control channel is sufficiently small such that actuation of the linked valve(s) through the valve controller does not substantially interfere with fluid flow in adjacent fluid channels. In a preferred embodiment, the valve arrangement in the multiplexer allows for the control of flow of material through each channel individually to allow each of the channels to be individually addressable by the opening and closing of a defined set of valves.

The direction of flow of material in the device is typically from at least one inlet port 11 to the outlet port 13. Flow of material through an inlet port 11 is controlled by a corresponding inlet valve 15 that is, in turn, controlled by a corresponding inlet valve control channel 16 via an inlet valve controller 17. Similarly, flow of material through an outlet port 13 is controlled by a corresponding outlet valve 19 that is, in turn, controlled by a corresponding outlet valve control channel 20 via a corresponding outlet valve controller 21. Each reaction unit includes at least one sacrificial channel 23 that is controlled by a corresponding sacrificial channel valve 25 that is, in turn, controlled by a corresponding sacrificial channel control channel 26 via a sacrificial channel valve controller 27. In a preferred embodiment, each reaction unit is bound by a pair of sacrificial channels, 23 one on each side. In a more preferred embodiment, the group of reaction units that comprise the device are further bound by a pair of sacrificial channels, 23' one on each side. Sacrificial channels as described herein are used to exchange fluid in the device so that the useable middle channels can be exposed to precise fluids at precise times. The sacrificial channels also ensure an even distribution of cells in the usable channels. Backflow of material through the device is controlled by a backflow prevention valve 29 that is, in turn, controlled by the backflow prevention control channel 30 via the backflow prevention valve controller 31.

Material can be introduced into each reaction unit individually through a reaction unit inlet port 33 that is controlled by a reaction unit inlet valve 35 that is controlled by an inlet valve control channel 36 that is, in turn, controlled by a reaction unit inlet valve controller 37. Similarly, material can be removed from each reaction unit individually through a reaction unit outlet port 39 that is controlled by a reaction unit outlet valve 38 that is controlled by an outlet valve control channel 40 that is, in turn, controlled by an outlet valve controller 41. In an alternative embodiment, all of the reaction unit inlet valves are not controlled by a single controller as shown in FIG. 1 (e.g., valves are controlled singly or in pairs). Similarly, and independently, a plurality of outlet valves need not be controlled collectively as shown in FIG. 1. In a device containing a plurality of reaction units, the units can be isolated from each other using the reaction unit inlet isolator valve 43, controlled by a reaction unit inlet isolator valve controller 45, and the reaction unit outlet isolator valve 47, controlled by a reaction unit outlet isolator valve controller 49. Controllers are operably linked to their corresponding valves via control channels. The device may include a reservoir for cell growth media that is functionally attached to an inlet port and an outlet port in the device (not shown). The device may also include an electric or re-circulating fluid device to maintain the temperature of the device (not shown).

Fluids can be introduced into the devices of the invention using modified syringes to which external air pressure can be applied. Fluids can be introduced into both fluid and control layers. Gas can be purged from fluid and control channels by hydrostatic pressure as the devices of the invention are gas permeable. The syringes are connected to Tygon tubing (Cole Palmer, ID 0.02"), and capped by a metallic tip tightly inserted into the chip inlet. Syringes are then mounted on a sliding platforms and fixed at different heights to control hydrostatic pressure at inlets and outlets. Plain water can be used for the valve control inlets.

Any of a number of methods of use of the device of the invention can be developed by those skilled in the art. The invention includes methods for the use of the device of the instant invention to practice methods including cell stimulation, staining, and/or visualization. For example, cells seeded in parallel fluid channels can be sequentially exposed to active agents in a time course fashion, and subsequently stained using immunofluorescence methods to analyze changes in protein expression and localization. A single active agent can be used for stimulation of all cells in the parallel reaction chamber, followed by immunostaining using multiple antibodies (e.g., immunostaining with two antibodies in all of the parallel fluid channels, or immunostaining with one or more antibodies in each of the individual reaction units). Alternatively, four different cell types can be seeded into the device, one per reaction unit, prior to cell stimulation and staining. Parallel fluid channels can be coated with various compounds to modulate cell adhesion prior to cell seeding. Cells can be stained using one or more antibodies as described above to determine changes in protein expression and localization in response to various cell adhesion substrates. In such a method, attachment of a fluid reservoir containing fresh media to the device would be preferred. Cells containing reporter constructs, either on plasmids or integrated into the genome of cells, can be analyzed using the devices and methods of the instant invention. Although the examples provided herein typically refer to immunostaining, it is understood that staining with fluorescent cell stains (e.g., DAPI, phalliodin, WGA), nucleic acid probes, reporter gene substrates for detecting reporter gene (e.g., beta-galactosidase, luciferase) expression, and other reagents, either alone or in combination with immunostaining, is within the scope of the invention.

The device of the invention is preferably for use with adherent cells. However, the device can be used with non-adherent cells by coating the interior of the parallel fluid channels with gelatin to promote cell adhesion. Primary or cultured cells may be used in the device. A major advantage of this device is that far fewer cells are needed than in other traditional experiments like Western blot or flow cytometry. The entire device as shown in FIG. 1 can be seeded with as few as 60,000 cells which allows for observation of about 3000-5000 cells in the end. In a preferred embodiment, the volume of a parallel reaction channel is about 70-80 nl. This small volume makes the device and methods of the invention ideal for use with primary cells, especially difficult to obtain primary cells (e.g., stem cells).

An exemplary device according to the instant invention is about 22×40 mm in area and about 4 mm thick (about the size of two thin stacks of quarters). In an embodiment, the device is the same size as a standard tissue culture slide to facilitate use in an automated microscopy device. However, the length and/or width of the device can be modified. Moreover, the number of channels and groups can be increased or decreased depending on the experiments to be performed. Due to the relative ease and low cost of fabrication of the device of the invention, multiple embodiments of the device can be made for use by a single laboratory. For example, the number of parallel reaction channels can be increased. This would allow for a larger number of stimuli and/or drugs to be screened across a larger number of cell types. Additionally, or alternatively, the number of inlets and outlets could be increased to allow for complex temporal patterns involving multiple stimuli or drugs.

EXAMPLES

It should be appreciated that the invention should not be construed to be limited to the examples that are now described; rather, the invention should be construed to include any and all applications provided herein and all equivalent variations within the skill of the ordinary artisan.

Example 1

Fabrication of a Device for High-Throughput Stimulation, Immunostaining and Visualization of a Single Cell The device was made using standard soft lithography techniques. The method of fabrication of the device is not a limitation of the invention.

Elastomeric devices have been developed for use in biological studies (for review see Sia and Whitesides 2003. *Electrophoresis* 24:3563-3576). Such devices are can be biocompatible and can be prepared relatively easily and inexpensively by methods well known to those skilled in the art (See e.g., reviews Whitesides et al., 2001. *Ann. Rev. Biomed. Eng.* 3:335-373, incorporated herein by reference). Elastomeric devices made by the process of soft lithography are produced by casting of polydimethylsulfoxide (PDMS) or other silicone rubber onto micromachined molds or coated silicone wafers patterned using contact lithography; however, other materials and methods can be used.

Briefly, for fabrication of the device of FIG. 1, the fluid and control layers were separately printed at 100% and 101.6% scale, respectively, at high resolution onto transparencies to create a mask. The increased size of the control layer mask accounts for PDMS cast shrinkage curing the fabrication procedure. The precise magnification may vary of the depending on the exact materials and methods used for fabrication of the device. Such modifications are well within the ability of those skilled in the art. Each mask was applied to a silicon wafer coated with photoresist and exposed to UV light, thereby transferring the pattern onto wafer by contact lithography. For elevated structures, positive photoresist is applied to the wafer, and exposed areas are removed using a chemical developer. For relatively tall structures, a negative mask and negative photoresist used and unexposed areas are removed using a chemical developer.

For the fluid layer, exposed areas of a positive photoresist were removed by a chemical developer, leaving ridges on the wafer in the form of the original pattern. A thermally reflowable photoresist, such as SJR5470, S1813, or SPR-220-7.0 were used so that the patterned photoresist could be heated to give a rounded contour. Fluid flow through rounded channels is far more effectively controlled by the valves of the control layer than square or trapezoidal channels. For the control layer, a negative mask and the negative photoresist SU-8 were used so that tall features could be created. The unexposed areas were removed by a chemical developer to leave ridges in the desired pattern.

Using the method of Unger et al. (2000) elastomeric layers can be readily assembled to create channels in a first, bottom "flow layer" that can be regulated by elastomeric valves in a second, top "control layer." Valves are created where a control channel in the control layer crosses a fluid channel in the fluid layer. The thin membrane between the two channels can be deflected by hydraulic actuation using a syringe or other device. When pressure is applied by passing air or other pressurized fluid through a control channel within the control layer, the membrane deflects downward to close off flow in the flow channel. Because the width of the control channel can be varied, and membrane deflection depends on dimensions, it is possible to have a control channel pass over a number of flow channels and actuate only a selection of flow channels. Tolerance in channel and valve sizes is largely dependent on ratios between the width of the valve/control channel and the fluid channel. Such considerations are well known to those skilled in the art. Guidance regarding the tolerance of the size of fluid channels, control channels, and valves can be found in Stunder et al. (2004 *J Appl. Phys.* 95: 393-398). Using such a layered design, miniaturized, elastomeric, computer-controlled microfluidics devices have been developed. Thorsten et al. (2002, *Science* 298:580-584).

The layers of the device were prepared using different ratios of PDMS to curing agent to facilitate the assembly of the final device. PDMS polymer mixed with a curing agent at a 5:1 ratio was cast thickly (about 4 mm) onto the control layer mold, and PDMS mixed with a curing agent at a 20:1 ratio was spincast thinly (about 50 um) onto the fluid layer mold. Both casts were partially cured to create grooves and channels in the desired patterns. The control layer PDMS cast was then drilled to create valve controller openings, cleaned, and assembled onto the fluid layer PDMS cast. The two layers were bonded to each other by further curing. The resulting monolithic PDMS slab was drilled to create inlet and outlet ports, cleaned and reversibly bonded to glass to create the final device with the control layer on top of the fluid layer, and the fluid layer attached to the glass with the fluid channels adjacent to the glass. This allows for removal of the glass to facilitate cleaning of the device so that it can be cleaned, rebounded to glass, and reused.

Example 2

Cell Culture, Stimulation, and Immunofluorescence Staining

The device was fabricated as described in Example 1. The device was filled with sterile 0.1% gelatin with all of the valves open through an inlet port 11 to coat the parallel fluid channels to promote cell adhesion. Valves were primed with filtered, distilled water. Alternatively, filling may be done with the ports closed as trapped air can be pushed out of the gas-permeable PDMS with hydrostatic pressure. The device was flushed with to remove the coating agent. Well-separated NIH3T3 mouse fibroblasts at a concentration of about 9 million cells per ml were introduced into the parallel fluid channels through an inlet port and the device was transferred to a standard 5% $CO_2$, 37° C. cell culture incubator for 3-4 hours to allow the cells to adhere to the glass bottom of the parallel fluid channels. Cells were observed at various time points after seeding and were found to be viable and have normal morphology for at least 15 hours in the absence of introduction of fresh media.

Using the multiplexer to control flow through the reaction units, a selection of valves were closed to allow for exposure of only a portion of the cells to a stimulant. A syringe containing a solution of 10 ng/ml of mouse TNF-alpha in media was attached to an inlet port, and cells were stimulated, or not, for 10 minutes. Cells that were not stimulated either had no fluid exchange whatsoever during the stimulation period, or fluid was exchanged for a fresh media without TNF-alpha in a manner identical to cell stimulation (mock stimulation). Before each subsequent step, the device is flushed with DPBS to remove the chemical agent form the preceding step. After stimulation, all valves in the multiplexer were opened, and cells were fixed by introducing a solution of 4% paraformaldehyde (PFA) in Dulbecco's phosphate buffered solution (DPBS) through an inlet port. Fixation lasted 20 minutes. In a similar manner, cells were permeablized for 5 minutes in 0.1% (v/v) Triton X-100 in DPBS, blocked for 1 hour in 10% goat serum in PBS (blocking solution), and stained for one hour with an anti-p65 antibody diluted in blocking solution and secondarily stained for one hour with a Texas Red- or Alexa Fluor-conjugated secondary antibody diluted in blocking solution. After secondary antibody staining and washing with DPBS, cells were overlaid with mounting media or other antifade agent to minimize photobleaching, and imaged using fluorescence microscopy. Such methods are well known to those skilled in the art. Control cells grown on slides were subjected to the same cell stimulation and staining protocols for comparison.

Cells in the device had identical patterns of localization of p65 as those on control slides. Hence, conditions inside the device are equivalent to those on slides. TNF-alpha treatment resulted in localization of p65 to the nucleus as expected. Translocation of p65 to the nucleus occurs in response to a number of cell stressors. Moreover, it was noted that even in mock stimulated cells, p65 was excluded from the nucleus. This indicates that the cells were not stressed by fluid exchange or other general conditions in the device.

Example 3

Detailed 32-Point Timecourse of the Response of One or More Proteins to Persistently Applied Stimulus or Drug The method is most readily accomplished using a device having four reaction units with eight parallel fluid channels per reaction unit such as the device shown in FIG. 1. A device can be readily fabricated to allow for variation in the number of reaction units and parallel fluid channels. The device was flushed with DPBS before each step to remove the chemical agent form the preceding step.

The device was coated the device with an agent that promotes cell adherence (e.g. gelatin, poly L-lysine, fibronectin, collagen, etc.). Cells were introduced into the device and allowed to adhere. Unattached cells were removed by flushing the parallel fluid channels with media. Valves were primed with filtered distilled water and flow is shut off all channels. Media containing an active agent was introduced into the device via any of the main inlets. The multiplexer was actuated so that the active agent was introduced to each channel at a different time (32 time points). Alternatively, the active agent may be released into multiple parallel fluid channels to so that the experiment is performed in duplicate (16 time points) or triplicate (10 time points) as desired. Time for introduction of the active agent was staggered so that each channel is exposed for a desired period with the exposure times all ending at the simultaneously. At this endpoint, the device was flushed with ice-cold DPBS, the cells were fixed and/or permeabilized in situ using desired reagents and methods, such as those provided above. Cells were stained in situ using standard immunofluorescence techniques and visualized by microscopy. Staining can be performed with multiple antibodies simultaneously using methods well known to those skilled in the art.

Example 4

8-Point Timecourse of the Response of 4 Proteins to a Persistently Applied Stimulus or Drug The method is most readily accomplished using a device having four reaction units with eight parallel fluid channels per reaction unit such as the device shown in FIG. 1. A device can be readily fabricated to allow for variation in the number of reaction units and parallel fluid channels. The device was flushed with DPBS before each step to remove the chemical agent form the preceding step.

The device was prepared, cells are seeded, and valves are primed as described in Example 3. Media containing an active agent was introduced into the device via one of the inlet ports. The multiplexer was actuated so that stimulus was introduced to one parallel fluid channel in each reaction unit at each of the 8 time points. Time for introduction of the stimulus was staggered so that each channel was exposed for a desired period with the exposures times all ending at the simultaneously. At this endpoint, the device was flushed with ice-cold DPBS, the cells were fixed and/or permeabilized in situ using desired reagents and methods, such as those provided above. Inlet isolator valves, 43, were used to isolate each reaction unit, and reaction unit-specific inlets, 33, and outlets, 34 were used to apply a different antibody to each group. After incubation with the primary antibody, cells were washed using the reaction unit-specific inlets and outlets. Depending on the selection of secondary antibody, the antibody can be introduced to all of the reaction units simultaneously through a common inlet port 11 and removed through the common outlet port 13. If the use of multiple secondary antibodies is required or desired, antibodies can be introduced separately into each of the reaction units through the reaction unit-specific inlets and outlets as with the primary antibody. Cells were observed by microscopy in situ.

Example 5

8-Point Timecourse of the Response of One or More Proteins to a Persistently Applied Stimulus or Drug in Four Different Cell Types The method is most readily accomplished using a device having four reaction units with eight parallel fluid channels per reaction unit such as the device shown in FIG. 1. A device can be readily fabricated to allow for variation in the number of reaction units and parallel fluid channels. The device was flushed with DPBS before each step to remove the chemical agent form the preceding step.

The device was prepared for cell seeding as in Example 3. The inlet isolator valves, 43, were used to isolate each reaction unit, and reaction unit-specific inlet ports, 33, and outlet ports, 34 were used, to seed a different cell type into each reaction unit. Unattached cells are removed by flushing the parallel fluid channels with media, through either the reaction unit-specific inlet ports and outlet ports, or through a common inlet port 11 and outlet port 13. Valves were primed with filtered distilled water and flow was shut off all channels. Media containing an active agent was introduced into the device via any one the main inlets 11. The multiplexer was actuated so that the active agent is introduced to one parallel fluid channel in each reaction unit at each of the eight time points. Alternatively, the multiplexer is actuated so that the stimulus is introduced to two parallel fluid channels in each reaction unit at each of four time points to allow for the experiment to be run in duplicate. Time for introduction of the stimulus was staggered so that each channel is exposed for a desired period with the exposures times all ending at the simultaneously. At this endpoint, the device was flushed with ice-cold DPBS, the cells were fixed and/or permeabilized in situ using desired reagents and methods, such as those provided above. Cells were stained using a common antibody introduced through a common inlet port. Alternatively, cells can be stained with four separate antibodies introduced through reaction unit-specific inlet and outlet ports. Cells were observed by microscopy in situ.

Example 6

8-Point Timecourse of the Response of One or More Proteins to Four Different Persistently Applied Stimuli or Drugs The method is most readily accomplished using a device having four reaction units with eight parallel fluid channels per reaction unit such as the device shown in FIG. 1. A device can be readily fabricated to allow for variation in the number of reaction units and parallel fluid channels. The device was flushed with DPBS before each step to remove the chemical agent form the preceding step.

The device is prepared, cells were seeded, and valves are primed as described in Example 3. The inlet isolator valves, 43, were used to isolate each reaction unit, and reaction unit-specific inlets, 33, and outlets, 34 were used to apply media containing a different stimulus to each reaction unit. The multiplexer was actuated so that stimulus was introduced to one parallel fluid channel in each reaction unit at each of the 8 time points. Alternatively, the multiplexer can be actuated so that the stimulus is introduced to two parallel fluid channels in each reaction unit at each of four time points to allow for the experiment to be run in duplicate. Time for introduction of the stimulus was staggered so that each channel was exposed for a desired period with the exposures times all ending at the simultaneously. At this endpoint, the device was flushed with ice-cold DPBS, the cells were fixed and/or permeabilized in situ using desired reagents and methods, such as those provided above. Cells were stained using a common antibody introduced through a common inlet port. Alternatively, cells can be stained with four separate antibodies introduced through reaction unit-specific inlet and outlet ports. Cells were observed by microscopy in situ.

Example 7

8-Point Timecourse of the Response of One or More Proteins to Four Different Pulsatile Patterns of a Stimulus or Drug The method is most readily accomplished using a device having four reaction units with eight parallel fluid channels per reaction unit such as the device shown in FIG. 1. A device can be readily fabricated to allow for variation in the number of reaction units and parallel fluid channels. The device was flushed with DPBS before each step to remove the chemical agent form the preceding step.

The inlet isolator valves, 43, were used to isolate each reaction unit, and reaction unit-specific inlets, 33, and outlets, 34, were used to apply fluid with an active agent, fluid without an active agent, fixative, and DPBS respectively to each of the four reaction units. A pattern of pulses were used in each timecourse and the resulting pattern of fluids that were applied to each channel. Times of administration were staggered so that channels do not interfere with one another (e.g. different fluids are not applied to different channels at the same time). In this case, the experiment ended at a different time for each channel, so the fluid pattern included exposure to fixative then DPBS. After all channels were finished, cells were stained using a common antibody introduced through a common inlet port. Alternatively, cells can be stained with four separate antibodies introduced through reaction unit-specific inlet and outlet ports. Cells were observed by microscopy in situ.

Example 8

Response of One or More Proteins to a Persistently Applied Stimulus or Drug in the Presence of Various Cell Adhesion Molecules The methods above can be carried out in a device in which each reaction unit is coated with a different agent to modulate cell adhesion.

Example 9

Observation of Live Cells in Response to Stimulus

In lieu of fixing cells immediately after exposure to an active agent, cells can be maintained in media and observed over time. As detailed above, the device of the invention allows for substantial variation in the seeding and treatment of cells. After exposure of cells to a stimulus for a defined timecourse, parallel fluid channels are flushed with fresh growth media. Cells are observed over time for a response to the stimulus (e.g., change in morphology, migration, apoptosis). Such changes can most easily be observed using video microscopy with a motorized stage positioning device. Growth media can be changed periodically depending on the amount of time the cells are to be observed. At the end of the observation period, cells may be fixed and stained as desired.

Given the modular nature of the device, these experiments can be "mixed-and-matched" to a large degree. For example, the experiments in Examples 5 and 7 could be combined: seed two groups each with a different cell type, expose each pair to different concentrations of the same stimulus, measure eight timepoints, and probe with one antibody. Also, those experiments in which only one protein is measured could be changed so that multiple proteins are measured in each cell. This could be done by staining with distinguishable antibodies. Such modifications are well within the ability of those skilled in the art.

Incorporation By Reference

The contents of all references, patents, pending patent applications and published patents, cited throughout this application are hereby expressly incorporated by reference.

Equivalents

Those skilled in the art will recognize, or be able to ascertain using no more than routine experimentation, many equivalents to the specific embodiments of the invention described herein. Such equivalents are intended to be encompassed by the following claims.

What is claimed is:

1. A microfluidic device for in situ cell analysis, comprising:
   at least one reaction unit comprising at least one inlet port comprising an inlet channel functionally connected to a plurality of parallel channels through which flow of material is controlled by at least one valve;
   wherein the plurality of parallel channels comprising the at least one reaction unit is adapted to receive one or more materials through the inlet channel of the at least one inlet port and wherein the at least one or more materials comprises at least one cell;
   wherein the plurality of parallel channels are functionally connected to the inlet channel of the at least one inlet port at a common junction and branch into a plurality of useable channels in which cell analysis and testing is done and at least a pair of sacrificial channels constructed to equalize a distribution of cells in the plurality of useable channels, wherein each reaction unit is geometrically configured such that the plurality of useable channels is bound by at least one sacrificial channel on each side thereof.

2. The microfluidic device of claim 1, further comprising at least two reaction units, wherein the at least two reaction units are functionally connected to at least one inlet port that is in fluid communication with each of the at least two reaction units.

3. The microfluidic device of claim 2, wherein the at least two reaction units are each functionally connected to at least one inlet port that is in fluid communication with only one reaction unit.

4. The microfluidic device of claim 1, wherein the at least one reaction unit is functionally connected to at least one outlet port.

5. The microfluidic device of claim 1, further comprising a multiplexer comprising a plurality of channel valves each of which controls the flow of material through at least one parallel channel and/or multiple parallel channels that may or may not be adjacent to each other and may or may not be in a single reaction unit, and wherein the multiplexer allows for each of the parallel fluid channels to be individually addressable by opening or closing a defined set of channel valves.

6. The microfluidic device of claim 2, further comprising a pair of sacrificial channels functionally connected to the at least one inlet port that is in fluid communication with each of the at least two reaction units, wherein the at least two reaction units are bound by the pair of sacrificial channels, having one sacrificial channel on each side thereof.

7. The microfluidic device of claim 2, wherein the device comprises at least 32 parallel fluid channels and wherein the channels are incorporated into the at least two reaction units.

8. The microfluidic device of claim 1, wherein the reaction unit comprises at least 4 or 10 parallel fluid channels per reaction unit.

9. The microfluidic device of claim 1, further comprising an inlet port valve functionally coupled to the inlet port.

10. The microfluidic device of claim 1, further comprising an outlet port valve functionally coupled to the outlet port.

11. The microfluidic device of claim 1, further comprising a backflow prevention valve functionally coupled to at least one of the fluid channels in the reaction unit.

12. The microfluidic device of claim 1, wherein the valves are actuated by hydrostatic pressure.

13. The microfluidic device of claim 1, wherein the device is composed of a biocompatible material.

14. The microfluidic device of claim 1, wherein the device is optically clear.

15. The microfluidic device of claim 1, wherein the device is gas permeable.

16. The microfluidic device of claim 1, wherein the device is composed of an elastomer.

17. The microfluidic device of claim 1, wherein at least one cell reaction chamber is coated with a compound to modulate cell adhesion.

18. The device of claim 1 wherein the device is reversibly mounted to a coverslip.

19. The microfluidic device of claim 1, wherein for at least one reaction unit, the fluid channels are functionally connected to an outlet channel at a common junction.

* * * * *